United States Patent [19]

Hunter et al.

[11] 3,942,532
[45] Mar. 9, 1976

[54] BRAIDED SUTURE

[75] Inventors: Alastair Wilson Hunter; Darrell R. Thompson, both of Somerville, N.J.

[73] Assignee: Ethicon, Inc., Somerville, N.J.

[22] Filed: Aug. 15, 1974

[21] Appl. No.: 497,596

Related U.S. Application Data

[63] Continuation-in-part of Ser. No. 303,588, Nov. 3, 1972, abandoned.

[52] U.S. Cl................................ 128/335.5; 428/375
[51] Int. Cl.² ........................................ A61L 17/00
[58] Field of Search ......... 128/335.5; 161/175, 176; 117/139.5 F, 161 R

[56] References Cited

UNITED STATES PATENTS

| | | | |
|---|---|---|---|
| 3,527,650 | 9/1970 | Block............................ | 128/335.5 X |
| 3,694,257 | 9/1972 | Dumont......................... | 117/139.5 F |
| 3,754,069 | 8/1973 | Adams et al.................. | 128/335.5 X |
| 3,776,766 | 12/1973 | Smerz et al................ | 117/139.5 F X |
| 3,839,524 | 10/1974 | Adams et al.................. | 128/335.5 X |

*Primary Examiner*—Dalton L. Truluck
*Attorney, Agent, or Firm*—Wayne R. Eberhardt

[57] ABSTRACT

The tie-down characteristics of braided sutures are improved by applying to the surface thereof a polymeric ester of a dibasic acid and a glycol.

16 Claims, 3 Drawing Figures

BRAIDED SUTURE

BACKGROUND OF THE INVENTION

This application is a continuation-in-part of my co-pending U.S. application Ser. No. 303,588, filed Nov. 3, 1972 now abandoned.

The present invention relates to surgical sutures and more specifically to multifilament sutures. Braided polyester multifilament sutures have been used by many surgeons for their strength and lack of tissue reactivity. Other surgeons prefer to use waxed silk when a non-absorbable suture is required because of its excellent hand, ease of knotting, and ease of passage through tissue.

An important characteristic of sutures in deep wound surgery is the ease of sliding a single throw knot down the suture into place. This behavior, sometimes referred to as the "tie-down performance" may be evaluated subjectively by tying a suture around a suitable mandrel. A single throw knot is formed and while pulling on the two free ends, the knot is forced to slide along the suture. The roughness or smoothness of this sliding action is an important criterion of performance.

Uncoated braids such as a braided polyethylene terephthalate suture give a very rough, jerky behavior while sutures coated with TEFLON, as described in U.S. Pat. No. 3,527,650 and wax-coated braided silk sutures are very smooth. Fortunately, the roughness or smoothness of tie-down can be measured and assigned a numerical value that will enable one to predict performance in the hands of the surgeon without reliance upon the subjective test referred to in the preceding paragraph. A method of using an INSTRON Universal Testing Instrument to determine tie-down performance is described below.

The present invention is directed to improving the tie-down characteristics of a braided suture by applying a surface coating of a non-toxic and physiologically inert polymer that does not adversely affect the hand or tensile properties of the suture.

It has now been discovered that the tie-down performance of braided, twisted, or covered multifilament sutures may be improved (the roughness decreased) by applying to the surface thereof polyesters derived from the polymerization of lactones or obtained by esterifying low molecular weight glycols with a dimeric acid. Preferred coating compositions are polyesters characterized by a melting point above room temperature and have the formula:

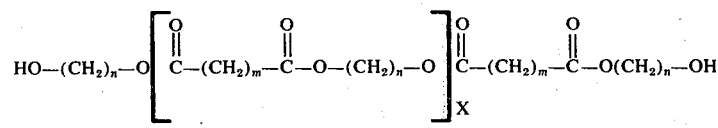

wherein $n$ is an integer larger than 1 and smaller than 13, $m$ is an integer larger than 1 and smaller than 9 and X is the degree of polymerization. Thus, stoichiometric quantities of succinic, glutaric, adipic, pimelic, suberic, azelaic, sebacic acid, or mixtures thereof may be condensed with ethylene glycol, propylene glycol, butanediol, pentanediol, hexanediol, nonanediol, decanediol, undecanediol, dodecanediol, or mixtures thereof to obtain a polyester suitable for application as a surface coating. Polyesters of the above formula having a molecular weight in the range of approximately 1,000 to 15,000 and characterized by having at least two carbon atoms between the ester linkages in the polymer chain have been found to give the best lubricant and handling properties on silk and polyester sutures. Particularly preferred polyesters are those derived from 1,4-butanediol ($n=4$) and adipic acid ($m=4$) having a molecular weight of 2,000–3,000.

It will be understood that branched chain acids such as $\alpha,\alpha,\beta$-trimethylsuberic acid having the formula:

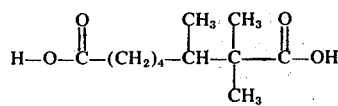

3,7-dimethyloctadienoic acid; 1,4-cyclohexanecarboxylic acid; mesatonic acid; $\beta,\beta$-dimethyl glutaric acid; and dimer acid; and branched chain diols such as diisononyl glycol having the formula:

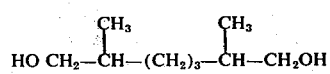

and glycols having a secondary hydroxyl group such as 1,2-propylene glycol may be added to the reaction mixture in small amounts as comonomers to produce polyesters suitable as coating materials that have a melting point above room temperature. The addition of larger amounts of such comonomers to the reaction mixture will result in low melting polyesters that are unsuitable for use in the present invention.

Polyesters that are useful in the manufacture of coated sutures in accordance with the present invention may also be prepared by polymerizing lactones. Such polyesters are characterized by a melting point above room temperature, and have the formula:

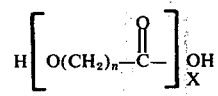

wherein $n$ is an integer larger than 2 and X is the degree of polymerization. Particularly preferred is the polyester characterized by a molecular weight of about 2,000 obtained by polymerizing $\epsilon$-caprolactones in the presence of a poly-methylenediol and having the formula:

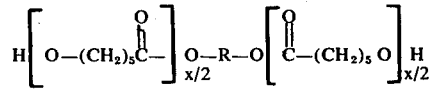

wherein R is a polymethylene group derived from the poly-methylenediol and $x$ is the degree of polymerization.

The polyester coating compositions described above are non-toxic and may be applied to the multifilament suture from solution. The multifilament suture may be of braided, twisted, or covered construction. The construction of a covered suture is described in U.S. Pat. No. 3,791,388. The suture is then air dried to remove solvent and form a continuous surface coating.

The amount of the polyester coating composition applied to the suture may be varied depending upon the suture size and composition. Thus, the surface coating on a size 710 braided polyester suture may amount to from about 5 percent to as much as 7 percent of the weight of the suture. Sutures of larger size (size 5/0 – 5) require a smaller amount of the polyester coating composition (about 0.4 percent to 1 percent based upon the weight of the suture).

The surface coating composition (0.4 percent to about 7 percent based on suture weight) has no detrimental effect on tensile strength or stability. While the application of an excess of the surface coating composition has an effect on lubricity, it may detract from other physical properties of the suture, particularly knot stability.

A numerical value may be assigned to the tie-down performance of any braided suture when tested in accordance with the following procedure. In describing the test for tie-down performance reference is made to the accompanying drawings wherein.

All tie-down measurements reported in the tables are made on a Table-Model INSTRON Tensile Tester using a Type B tension cell, full-scale range 100 to 2,000 grams. The INSTRON instrument is manufactured by the Instron Corporation of Canton, Massachusetts. A high-speed SANBORN Oscillographic Recorder (Model 7702A, manufactured by Hewlett-Packard, Waltham, Massachusetts) is substituted for the standard INSTRON Recorder which would be too slow to follow the rapid changes in force that result as the sutures under test slide against each other. A high-gain DC Amplifier (Hewlett-Packard Model 8803A, manufactured by Hewlett-Packard, Waltham Division, Waltham, Massachusetts) is used to interface this recorder with the INSTRON Transducer and a low-voltage DC power supply is provided to excite the transducer. The measurements are made in an air-conditioned laboratory at 72°F. and 50 percent relative humidity. To hold the specimen suture strands, a line contact jaw is used. The INSTRON machine is operated at a cross-head speed of 50 inches per minute and the chart speed of the oscillographic recorder is 20 millimeters per second.

Figure 1:
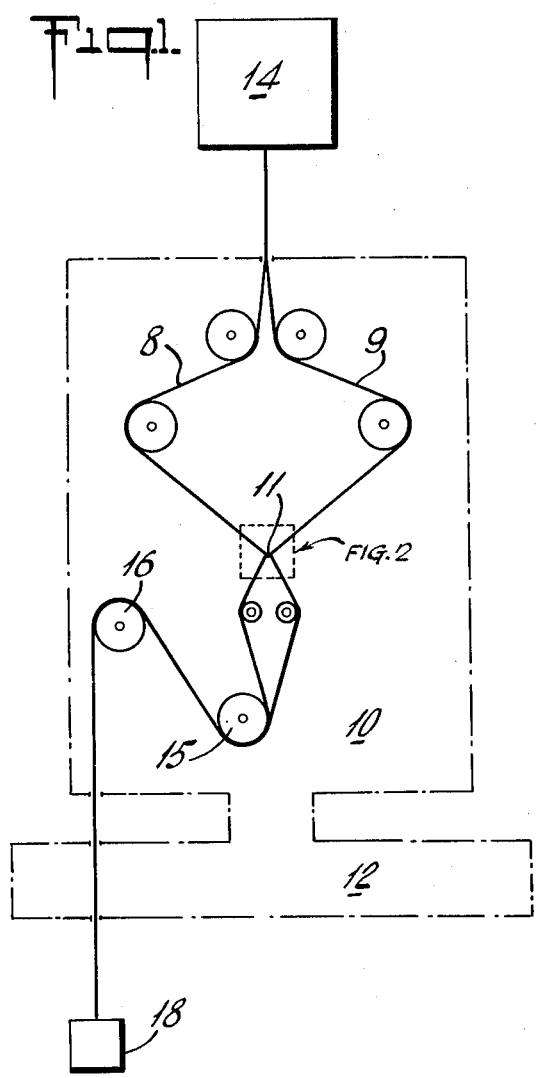
FIG. 1 is a diagrammatic representation of an INSTRON Tester and shows two braided suture strands in position for testing.
Figure 2:
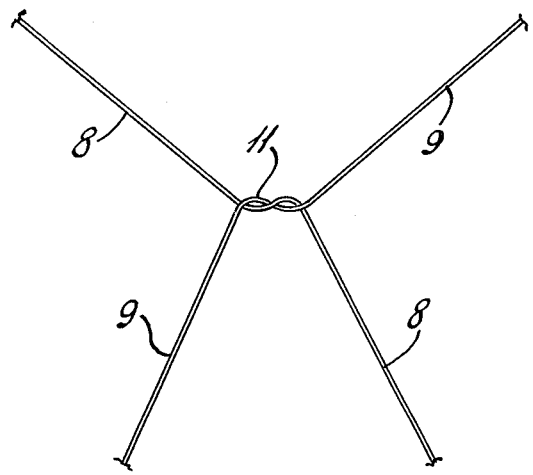
FIG. 2 is an enlarged perspective view of the single throw knot illustrated in FIG. 1.

Subjective tests for tie-down involved the suture configuration 11 shown in FIG. 2 (a single throw knot). The same configuration is produced by a pulley arrangement that is supported by a steel plate 10 shown in FIG. 1. The steel plate is attached to the cross-head 12 of the INSTRON Tester.

To perform tie-down measurements, two strands 8 and 9 of the same suture are attached at one end to the B cell transducer 14 of an INSTRON Tester. The sutures are threaded through the pulley arrangement as shown in FIGS. 1 and 2. The other end of the suture strands are brought together, passed around the pulleys 15 and 16, and attached together to a weight 18 which provides tension similar to that applied in a subjective test. A weight of 2.5 pounds is used in the standard procedure.

Figure 3:
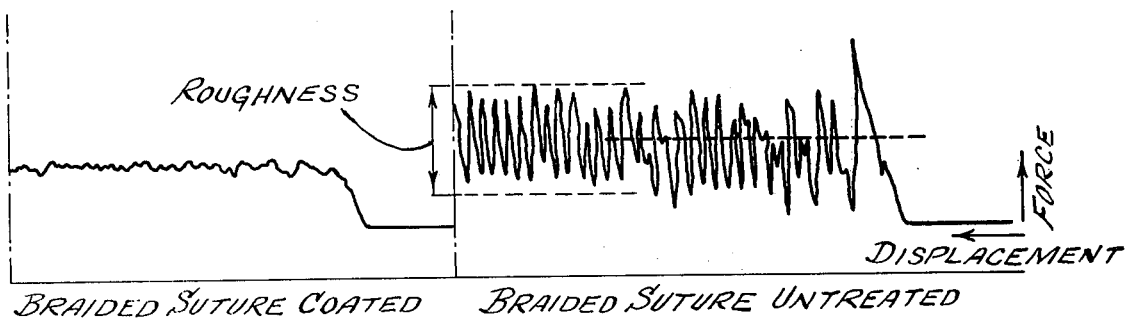
FIG. 3 is a reproduction of the tracing of an oscillographic recorder.

FIG. 3 shows actual recorder traces for a braided polyethylene terephthalate suture before and after coating with a polymer to improve tie-down performance. The roughness values are measured along the ordinate and throughout the specification and examples are recorded in pounds (roughness). When relatively smooth samples are compared, the amplitude of the oscillographic recorder can be increased by a factor of 20.

The present invention will be further illustrated by the following examples which illustrate preferred embodiments of the inventive idea.

EXAMPLE I

A condensation polymer is prepared by reacting 42.5 weight percent of 1,4-butanediol with 57.5 weight percent of adipic acid. The polymer so obtained is a firm, waxy solid having a viscosity of 1475 cps. at 60°C., a molecular weight of 2150, an acid number of 1.7, and a hydroxyl number of 52.1.

The polyester prepared as described in the preceding paragraph (4.84 parts by weight) is dissolved in 95.16 parts by weight of toluene and the solution is applied to a braided, size 2/0 polyethylene terephthalate suture strand using an ATLAB Yarn Finish Applicator manufactured by Precision Machine & Development Company, P.O. Box 645, New Castle, Delaware. The braid is coated under the following conditions:

| | |
|---|---|
| Speed of Yarn | 30 feet per minute |
| Hypodermic Syringe Size | 30 cc. |
| Motor Drive Rate | 10 r.p.m. |
| Hysteresis Tension | 5 pounds. |

The coated, braided strand is dried in forced air at 70°–80°F. to evaporate the solvent and is then collected on a take-up drum. No curing of the adipic ester is required. The coating is continuous over the entire surface of the suture and amounts to 1 percent by weight (based on the weight of the untreated suture). The coated braid is sterilized by exposure to cobalt-60 irradiation without significant loss of straight tensile strength or knot strength. The physical characteristics of the braided polyethylene terephthalate suture before and after coating are summarized in Table 1.

TABLE 1

| | Braided Size 2/0 Polyethylene Terephthalate Suture (Untreated) | Braided Size 2/0 Polyethylene Terephthalate Suture (Coated) |
|---|---|---|
| Tensile Strength | | |
| Non-Sterile | 100,200 p.s.i. | 99,100 p.s.i. |
| Sterile | 99,400 p.s.i. | 98,800 p.s.i. |
| Knot Strength | | |
| Non-Sterile | 53,900 p.s.i. | 53,500 p.s.i. |
| Sterile | 52,100 p.s.i. | 55,000 p.s.i. |

TABLE 1-continued

| | Braided Size 2/0 Polyethylene Terephthalate Suture (Untreated) | Braided Size 2/0 Polyethylene Terephthalate Suture (Coated) |
|---|---|---|
| Roughness | 3.67 lbs. | 0.31 lbs. |

Similar results are obtained when the polyester resin described in this Example is used to coat braided silk, cotton, and collagen sutures. However, higher levels of coating solids should be used for the hydrophilic substrates such as cotton and silk. The coated sutures made according to this example have excellent knot holding properties.

EXAMPLE II

A linear polymer of ε-caprolactone characterized by an average molecular weight of about 2,000 and having the structural formula:

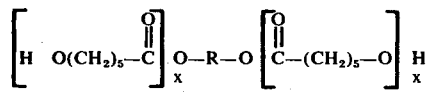

wherein R is a polymethylene group derived from a polymethylenediol and x represents the degree of polymerization, was purchased from the Union Carbide Corporation, Chemical Division, 270 Park Avenue, New York City, New York. This polycaprolactone has a molecular weight of about 2,000 and is sold under the trade name NIAX POLYOL D-560.

The polycaprolactone identified above was dissolved in toluene to obtain a 3.8 percent by weight solution. This solution is applied to a braided, size 2/0 polyethylene terephthalate suture strand using an ATLAB Yarn Finish Applicator. The braid is coated under the conditions as described in Example I above and dried in forced air at 75°F. The coated braid, after evaporation of the solvent is collected on a take-up drum. No curing of the polycaprolactone is required. The coating is continuous over the entire surface of the suture and amounts to 1 percent by weight (based on the weight of the untreated suture). The coated braid is sterilized by exposure to cobalt-60 irradiation without appreciable loss of straight tensile strength or knot strength. The physical characteristics of the braided polyethylene terephthalate suture before and after coating are summarized in Table 2.

TABLE 2

| | Braided Size 2/0 Polyethylene Terephthalate Suture (Untreated) | Braided Size 2/0 Polyethylene Terephthalate Suture (Coated) |
|---|---|---|
| Tensile Strength | | |
| Non-Sterile | 96,300 p.s.i. | 92,000 p.s.i. |
| Sterile | 95,100 p.s.i. | 91,500 p.s.i. |
| Knot Strength | | |
| Non-Sterile | 53,900 p.s.i. | 51,700 p.s.i. |
| Sterile | 54,700 p.s.i. | 51,700 p.s.i. |
| Roughness | 2.77 lbs. | 0.67 lbs. |

Similar results are obtained when the polycaprolactone is used to coat braided silk, cotton, and collagen sutures of size 2/0 through 6/0. The polyesters of the present invention may also be used to coat absorbable synthetic sutures such as those described in U.S. Pat. No. 3,297,033 and 3,636,956 with a resulting improvement in tie-down characteristics.

What is claimed is:

1. A suture having improved tie-down performance comprising a multifilament, the outer surface of the multifilament being coated with from about 0.4 percent to about 7 percent based on suture weight of an aliphatic polyester that is a solid at room temperature; said polyester having from 2 carbon atoms to about 12 carbon atoms between the ester linkages in the polymer chain and said polyester having a molecular weight in the range of 1,000 to 15,000.

2. The suture of claim 1, characterized by a braided construction.

3. The suture of claim 1, characterized by a twisted construction.

4. The suture of claim 1, characterized by a covered construction.

5. The multifilament suture of claim 1, wherein the polyester has the formula:

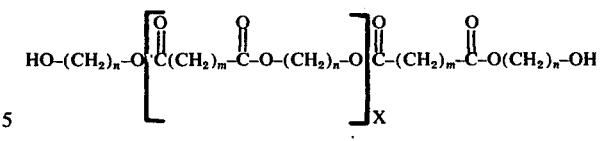

wherein n is an integer larger than 1 and smaller than 13, m is an integer larger than 1 and smaller than 9 and X is the degree of polymerization.

6. The multifilament suture of claim 1, wherein the polyester has the formula:

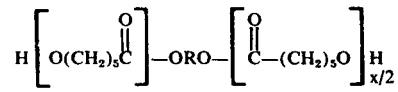

wherein R is a polymethylene group and X represents the degree of polymerization.

7. The multifilament suture of claim 1, wherein the polyester is a condensate of adipic acid and 1,4-butanediol having a molecular weight of about 2,000–3,000.

8. The suture of claim 7, wherein said multifilament is a silk multifilament and the polyester coating amounts to about 5 percent of the weight of the untreated suture.

9. The suture of claim 7, wherein said multifilament is a polyethylene terephthalate multifilament, and the polyester coating amounts to about 1 percent of the weight of the untreated suture.

10. The multifilament suture of cliam 6, wherein the polyester coating has a molecular weight of about 2,000.

11. The suture of claim 10, wherein said multifilament is a polyethylene terephthalate multifilament and the polyester coating amounts to about 1 percent of the weight of the untreated suture.

12. The suture of claim 10, wherein said multifilament is a silk multifilament and the polyester coating amounts to about 5 percent of the weight of the untreated suture.

13. The multifilament suture of claim 1, characterized by a roughness of less than 1 pound.

14. The multifilament suture of claim 2, characterized by a roughness of less than 1 pound.

15. The multifilament suture of claim 3, characterized by a roughness of less than 1 pound.

16. The multifilament suture of claim 4, characterized by a roughness of less than 1 pound.

* * * * *

UNITED STATES PATENT AND TRADEMARK OFFICE
CERTIFICATE OF CORRECTION

PATENT NO. : 3,942,532
DATED : March 9, 1976
INVENTOR(S) : Hunter, Alastair Wilson & Thompson, Darrell R.

It is certified that error appears in the above-identified patent and that said Letters Patent are hereby corrected as shown below:

In Column 3, Line 8, the word "710" should read --- 7/0 ---.

In Column 5, Line 24, the word " [H" should read --- H[ ---.

In Column 5, Line 25, the word "X" should read --- X/2 ---.

In Column 7, Line 8, the word "cliam" should read --- claim ---.

In Column 6, Line 45, the formula in claim 6 should have x/2 after first bracket.

Signed and Sealed this

Second Day of November 1976

[SEAL]

Attest:

RUTH C. MASON
*Attesting Officer*

C. MARSHALL DANN
*Commissioner of Patents and Trademarks*